United States Patent [19]

Na et al.

[11] Patent Number: 5,447,710
[45] Date of Patent: Sep. 5, 1995

[54] METHOD OF MAKING NANOPARTICULATE X-RAY BLOOD POOL CONTRAST AGENTS USING HIGH MOLECULAR WEIGHT NONIONIC SURFACTANTS

[75] Inventors: George C. Na, Fort Washington; Natarajan Rajagopalan, Phoenixville, both of Pa.

[73] Assignee: Eastman Kodak Company, Rochester, N.Y.

[21] Appl. No.: 242,492

[22] Filed: May 13, 1994

Related U.S. Application Data

[62] Division of Ser. No. 991,909, Dec. 17, 1992, Pat. No. 5,326,552.

[51] Int. Cl.⁶ .......................... A61K 49/04; A61K 9/14
[52] U.S. Cl. .................... 424/9.455; 424/489; 424/499; 424/9.4; 514/5; 514/718; 514/975
[58] Field of Search ............... 424/5, 4, 489, 499; 514/5, 718, 975

[56] References Cited

U.S. PATENT DOCUMENTS

| 4,406,878 | 9/1983 | DeBoer ..................................... 424/5 |
| 4,540,602 | 9/1985 | Motoyama et al. ............. 427/213.31 |
| 5,141,703 | 5/1992 | Wolf et al. ................................ 424/5 |
| 5,145,684 | 9/1992 | Liversidge et al. ................. 424/489 |

FOREIGN PATENT DOCUMENTS 498482  8/1992  European Pat. Off. .

*Primary Examiner*—Gary E. Hollinden
*Attorney, Agent, or Firm*—Arthur H. Rosenstein

[57] ABSTRACT

The present invention is directed to a composition comprised of nanoparticles containing an x-ray diagnostic compound, having a high molecular weight nonionic surfactant as a surface modifier adsorbed on the surface thereof and a cloud point modifier associated therewith.

The present invention is also directed to a method for making nanoparticles comprising (i) contacting said nanoparticle containing an x-ray diagnostic compound with a high molecular weight nonionic surfactant for a time and under conditions sufficient to form a nanoparticle with the surfactant adsorbed on the surface thereof; and (ii) contacting the so treated nanoparticle with a cloud point modifier for a time and under conditions sufficient to form a nanoparticle containing an x-ray diagnostic compound, having a nonionic surfactant as a surface modifier adsorbed on the surface thereof and a cloud point modifier associated therewith.

The present invention is still further directed to a method for diagnostic imaging for use in medical procedures comprising administering to the body of a test subject in need of an x-ray an effective contrast producing amount of a composition comprised of nanoparticles containing an x-ray diagnostic compound, having a high molecular weight nonionic surfactant as a surface modifier adsorbed on the surface thereof and a cloud point modifier associated therewith.

17 Claims, No Drawings

METHOD OF MAKING NANOPARTICULATE X-RAY BLOOD POOL CONTRAST AGENTS USING HIGH MOLECULAR WEIGHT NONIONIC SURFACTANTS

This application is a division of application Ser. No. 07/991,909, filed Dec. 17, 1992, U.S. Pat. No. 5,326,552.

FIELD OF THE INVENTION

The present invention relates to X-ray imaging compositions with a surfactant adsorbed thereto, and a method for making and using same.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on contrast agents and media in medical imaging is provided by D. P. Swanson et al., Pharmaceuticals in Medical Imaging, 1990, MacMillan Publishing Company.

Briefly, in x-ray imaging, transmitted radiation is used to produce a radiograph based upon overall tissue attenuation characteristics. X-rays pass through various tissues and are attenuated by scattering, i.e., reflection or refraction or energy absorption. However, certain body organs, vessels and anatomical sites exhibit so little absorption of x-ray radiation that radiographs of these body portions are difficult to obtain. To overcome this problem, radiologists routinely introduce an x-ray absorbing medium containing a contrast agent into such body organs, vessels and anatomical sites.

Maximum enhancement of major blood vessels takes place during the so-called vascular phase of contrast media kinetics which occurs within about the first two minutes following the intravascular infusion or bolus injection of the contrast media. This is because the plasma concentration of an intravascular contrast medium decreases rapidly as a result of vascular mixing, transcapillary diffusion of the medium from the circulation into the interstitial spaces and renal excretion. Consequently, imaging of blood vessels must take place within a narrow time window, typically within a few minutes after infusion or injection of the x-ray contrast agent.

It would be desirable to provide improved x-ray contrast compositions for imaging vessels, anatomical sites and body organs such as the liver and spleen. Moreover, it would be highly desirable to provide intravenously administered x-ray contrast compositions which demonstrate effective imaging of the blood pool for extended periods of time.

Surface modified crystalline nanoparticles of water-insoluble x-ray contrast agents provide images of exceptional resolution and can be formulated for enhanced delivery to specific tissue or fluid sites, e.g., the blood pool, liver, kidney, bone marrow, lymph nodes and spleen. Moreover, preferred x-ray contrast agents when administered intravenously provide effective imaging of the blood pool within the vascular system for remarkably long periods of time.

Nanoparticles were first described in U.S. Pat. No. 5,145,684. These particles consist of a crystalline drug substance having a surface modifier adsorbed on the surface of the particles such that the average particle size is less than about 400 nm.

Iodine-containing agents in the nanoparticulate form dispersed with only Tetronic surfactant T-908 can remain in the blood pool for hours and give satisfactory imaging results.

However, in order to achieve autoclave sterilization of the suspension, an anionic surfactant such as dioctylsulfosuccinate (DOSS) or anionic phospholipid such as dimyristoylphosphatidylglycerol (DMPG) is often required. However, the charges imparted by the ionic surfactant/phospholipid lead to faster excretion of the drug substance and poor imaging results.

The blood residence time of intravenously injected nanoparticles is inversely related to the zeta potential of the nanodispersion. Nanoparticles with strong zeta potential tend to be cleared from the blood sooner, presumably by the reticuloenodthelial system (RES) system.

To overcome this charge effect, the zeta potential of nanoparticles dispersed with various surfactants, including those of the Tetronic series, were tested. It was noticed that the zeta potentials of nanoparticles dispersed with the Tetronic series of surfactants in the presence of DOSS or DMPG are inversely related to the molecular weight of the surfactants, i.e. higher molecular weight surfactants showed lower (absolute value) of zeta potentials and thus stronger ability to mask the charges on the particle.

These results led to the concept of using higher molecular weight surfactant to overcome the charge effect imparted by the ionic species added to the formulation. When tested with ethyl 3,5-diacetoamido-2,4,6-triiodobenzoate (WIN-8883), T-1508, the highest molecular weight surfactant in the Tetronic series, gave the lowest zeta potential nanoparticles in the presence of either DOSS or DMPG.

BRIEF SUMMARY OF THE INVENTION

The present invention is directed to a composition comprised of nanoparticles containing an x-ray diagnostic compound, having a high molecular weight surfactant as a surface modifier adsorbed on the surface thereof and a cloud point modifier associated therewith.

A preferred x-ray diagnostic compound is ethyl 3,5-diacetoamido-2,4,6-triiodobenzoate (WIN 8883).

A preferred non-ionic poloxamer surfactant is a poloxamine. A particularly preferred poloxamine is Tetronic-1508.

Preferred nonionic cloud point modifiers include polyethylene glycols, propylene glycol, ethanol, and cyclodextrin. Preferred ionic cloud point modifiers include ionic surfactants, e.g., sodium dodecyl sulfate, dioctylsulfosuccinate, and cetrimide, and charged phospholipids, e.g., dimyristoylphosphatidylglycerol, cardiolipin, and dimyristoylphosphatidylserine.

The present invention is also directed to a method for making nanoparticles containing an x-ray diagnostic compound, having a high molecular weight surfactant as a surface modifier adsorbed on the surface thereof and a cloud point modifier associated therewith comprising the steps of:

(i) contacting said nanoparticle containing an x-ray diagnostic compound with said high molecular weight surfactant for a time and under conditions sufficient to form a nanoparticle with a surface modifier adsorbed on the surface therof; and (ii) contacting the nanoparticle of step (i) with a cloud point modifier for a time and under conditions sufficient to form a nanoparticle containing an x-ray diagnostic compound, having a high molecular weight surfactant as a surface modifier adsorbed on the surface thereof and a cloud point modifier associated therewith.

In another embodiment of this invention, there is provided a method for making nanoparticles containing an x-ray diagnostic compound having a high molecular weight non-ionic surfactant, e.g., a poloxamine surfactant having a molecular weight of at least about 30,000, as a surface modifier adsorbed on the surface thereof comprised of contacting the nanoparticle containing an x-ray diagnostic compound with a high molecular weight nonionic surfactant for a time and under conditions sufficient to form a nanoparticle with the surface modifier adsorbed on the surface thereof.

The present invention is still further directed to a method for diagnostic imaging for use in medical procedures comprising administering to the body of a test subject in need of an x-ray an effective contrast producing amount of a composition comprised of nanoparticles containing an x-ray diagnostic compound, having a high molecular weight surfactant as a surface modifier adsorbed on the surface thereof and a cloud point modifier associated therewith.

DETAILED DESCRIPTION OF THE INVENTION

The present invention is directed to an x-ray contrast composition comprising particles consisting essentially of a non-radioactive crystalline organic x-ray contrast agent having a high molecular weight surface modifier adsorbed on the surface thereof in an amount sufficient to maintain an effective average particle size of less than 400 nm, and a cloud point modifier associated therewith.

The x-ray contrast composition of this invention comprises particles of an organic x-ray contrast agent having a surface modifier adsorbed on the surface thereof in an amount sufficient to maintain an effective average particle size of less than 400 nm.

The x-ray contrast agent useful in the practice of this invention is non-radioactive and exists as a discrete, crystalline phase of an organic substance. The crystalline phase differs from an amorphous or non-crystalline phase which results from solvent precipitation techniques such as described in U.S. Pat. No. 4,826,689 noted above. The organic substance can be present in one or more suitable crystalline phases. The invention can be practised with a wide variety of crystalline, non-radioactive x-ray contrast agents. However, the x-ray contrast agent must be poorly soluble and dispersible in at least one liquid medium. The phrase "poorly soluble", as used herein means that the agent has a solubility in the liquid dispersion medium, e.g., water, of less than about 10 mg/ml, and preferably of less than about 1 mg/ml. The preferred liquid dispersion medium is water. Additionally, the invention can be practised with other liquid media in which the selected x-ray contrast agent is poorly soluble and dispersible, including, for example, aqueous saline solutions, such as phosphate buffered saline (PBS), plasma, mixed aqueous and nonaqueous solutions, for example, water and alcohol, and suitable nonaqueous solvents such as alcohol, glycerol and the like.

A particularly preferred x-ray contrast agent is ethyl 3,5-diacetoamido-2,4,6-triiodobenzoate (WIN-8883).

The particles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages, As used herein, the term "high molecular weight nonionic surfactant" means any surfactant with a molecular weight above 4000. Preferred high molecular weight surface modifiers (surfactants) are non-ionic with polyethylene oxide (PEG) chain(s) as the hydrophilic segment. Particularly preferred surfactants contain one or more polyethylene glycol (PEG) chains constituting the hydrophilic segment of the molecule with a molecular weight above 4000 for the PEG chain. The hydrophobic segment of the surfactant can be an alkyl, acyl, alkylphenol, polypropyleneoxide, or diacylphosphatidyl group. Surfactants with polypropyleneoxide segment include poloxamines such as Tetronic 908 and Tetronic 1508 (also known as poloxamine 908 and poloxamine 1508), which are tetrafunctional block copolymers derived from sequential addition of propylene oxide and ethylene oxide to ethylenediamine, available from BASF. Surfactants with an alkylphenol group as the hydrophobe include NP-100 and NP-70 available from BASF. Surfactants with a diacylphosphatidyl group as the hydrophobe include diapalmitylphosphatidylethanolaminepolyethyleneoxide-5000 available from Avanti. Preferred surfactants have a molecular weight above 4000. The most preferred surfactants have a molecular weight above 5000. For example, preferred surfactants can contain one or more polyethylene oxide chains having a molecular weight above 4000, and more preferably above 5000. Preferred surface modifiers can be selected from known non-ionic surfactants, including the poloxamines such as Tetronic 908 (also known as Poloxamine 908), which is a tetrafunctional block copolymer derived from sequential addition of propylene oxide and ethylene oxide to ethylenediamine, available from BASF, or Tetronic 1508 (T1508).

The surface modifiers are commercially available and/or can be prepared by techniques known in the art. Two or more surface modifiers can be used in combination.

The x-ray contrast compositions of this invention comprise the above-described particles and a carrier therefor. For example, the particles can be dispersed in an aqueous liquid which serves as the carrier for the x-ray contrast agent. Other suitable carriers include liquid carriers such as mixed aqueous and nonaqueous solvents, for example water and alcohols, and suitable nonaqueous solvents, such as alcohol; gels; gases, such as air; and powders. The x-ray contrast composition can comprise from about 1–99.9, preferably 2–45 and more preferably 10–25 percent by weight of the above-described particles, the remainder of the composition being the carrier, additives and the like. Compositions up to about 100 percent by weight of the particles are contemplated when the composition is in a lyophilized form.

The nanoparticles useful in the practice of this invention can be prepared according to the methods disclosed in U.S. Pat. No. 5,145,684, whose disclosure is incorporated herein by reference. A general procedure for preparing the particles useful in the practice of this invention follows. The diagnostic agent selected is obtained commercially and/or prepared by techniques known in the art as described above, in a conventional coarse form. It is preferred, but not essential, that the particle size of the coarse diagnostic substance selected be less than about 100 μm as determined by sieve analysis. If the coarse particle size of that agent is greater than about 100 μm, then it is preferred that the coarse particles of the diagnostic agent be reduced in size to less than 100 μm using a conventional milling method such as airjet or fragmentation milling.

The coarse diagnostic agent selected can then be added to a liquid medium in which it is essentially insoluble to form a premix. The concentration of the diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm3. Zirconium oxide, such as 95% ZrO stabilized with magnesia, zirconium silicate, and glass grinding media provide particles having levels of contamination which are believed to be acceptable for the preparation of diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm2) are typical of media milling.

The surface modifier, and the cloud point modifier, if not present in the premix, can be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of diagnostic agent and surface modifier can vary widely and the optimal amount of the surface modifier can depend, for example, upon the particular diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the diagnostic agent. The surface modifier can be present in an amount of 0.1–90%, preferably 1–75%, more preferably 10–60%, and most preferably 10–30% by weight based on the total weight of the dry particle.

The cloud point modifier can be present in an amount of about 0.01–20%, preferably 0.05–10%, and most preferably 0.1–10%.

Diagnostic agents useful in the composition of the present invention include those disclosed in U.S. Pat. No. 5,145,684, whose disclosure is incorporated herein by reference, and EP-A 498,492. A preferred diagnostic agent is the x-ray imaging agent WIN-8883 (ethyl 3,5-diacetoamido-2,4,6-triiodobenzoate).

As used herein, particle size refers to an average particle size as measured by conventional particle size measuring techniques well known to those skilled in the art, such as sedimentation field flow fractionation, photon correlation spectroscopy, or disk centrifugation. The phrase "an effective average particle size of less than about 400 nm" as used herein means that at least 90% of the particles have a particle size of less than about 400 nm when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

A method for the preparation of a nanoparticle composition according to this invention includes the steps of introducing a diagnostic agent, a liquid medium, grinding media, and optionally, a surface modifier into a grinding vessel; wet grinding to reduce the particle size of the diagnostic agent to less than about 400 nm; and separating the particles and optionally the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions. Thereafter, the nanoparticle composition preferably is subjected to a sterilization process.

Sterilization can take place in the presence of anionic surfactants such as dioctylsulfosuccinate (DOSS) or anionic phospholipids such as dimyristol phosphatidyl glycerol (DMPG).

The cloud point is the temperature at which the surface modifier (surfactant) precipitates out of solution as described above. Anionic surfactants and anionic phopholipids act as cloud point modifiers. The phrase "cloud point modifier" as used herein means a compound which influences the cloud point of surface modifiers. In particular, the cloud point modifiers useful in the present invention raise the cloud point of the surface modifiers found adsorbed onto nanoparticles. In this way, the surface modifiers do not dissociate from the surface of the nanoparticles at temperatures used in autoclaving. Therefore, nanoparticles thus modified do not agglomerate during the sterilization process, and thus retain their effective average particle sizes of less than about 400 nm after sterilization.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5-20 mgI/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of the tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like. In addition to the preferred applications discussed above, i.e., for blood pool, liver, spleen and lymph node imaging, the x-ray contrast compositions of this invention are also expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

Effect of various molecular weight tetronic surfactants in masking the charge (zeta potential) of nanoparticles imparted by the charged phospholipid DMPG. Nanoparticulate suspensions contained 5% WIN-8883, 0–2% DMPG. 0.5 mL of suspension was added 0.075 mL of 20% stock solution of a testing surfactant. The final concentration of the surfactant was 3%.

| Surfactant | MW | Zeta Potential (mV) |
| --- | --- | --- |
| none | — | −51 |
| T-707 | 12200 | −20 |
| T-908 | 25000 | −18 |
| T-909 | 30000 | −11 |
| T-1107 | 15000 | −25 |
| T-1107 | 15000 | −22 |
| T-1307 | 18000 | −14 |
| T-1508 | 30000 | −6 |

Effect of various molecular weight tetronic surfactants in masking the charge (zeta potential) of nanoparticles imparted by the anionic surfactant dioctylsulfosuccinate (DOSS). Nanoparticulate suspensions contained 15% WIN-8883, 0.2% DOSS. 0.5 mL of suspension was added 0.075 mL of 20% stock solution of a testing surfactant. The final concentration of the surfactant was 3%.

| Surfactant | MW | Zeta Potential (mV) |
| --- | --- | --- |
| none | — | −6 |
| T-707 | 12200 | −0.5 |
|  |  | −0.4 |
| T-908 | 25000 | −0.4 |
|  |  | −1.4 |
| T-909 | 30000 | −0.6 |
| T-1107 | 15000 | −0.9 |
| T-1307 | 18000 | −0.8 |
| T-1508 | 30000 | 0.2 |

Effect of various molecular weight alkylphenol-polyethoxylate surfactants in masking the charge (zeta potential) of nanoparticles imparted by the charged phospholipid (DMPG). Nanoparticulate suspensions contained 15% WIN-8883, 0.2% DOSS. 0.5 mL of suspension was added 0.075 mL of 20% stock solution of a testing surfactant. The final concentration of the surfactant was 3%.

| Surfactant | MW | Zeta potential (mV) |
|---|---|---|
| OP-10 | 550 | −45.81 |
| OP-30 | 1530 | −37.40 |
| OP-40 | 2000 | −34.93 |
| NP-50 | 2500 | −27.66 |
| NP-70 | 3300 | −25.50 |

The foregoing specification, including the specific embodiments and examples is intended to be illustrative of the present invention and is not to be taken as limiting. Numerous other variations and modifications can be effected without departing from the true spirit and scope of the present invention.

We claim:

1. A method for making nanoparticles containing an x-ray diagnostic compound, having a non-ionic surfactant having a molecular weight of at least 4000 as a surface modifier adsorbed on the surface thereof in an amount of 1 to 75% by weight based on the total weight of the particle and a cloud point modifier associated therewith present in an amount of 0.01–20% by weight based on the total weight of the composition, said method comprised of (i) contacting said nanoparticle containing an x-ray diagnostic compound with said non-ionic surfactant for a time and under conditions sufficient to form a nanoparticle with a surface modifier adsorbed on the surface thereof; and (ii) contacting said nanoparticle with a surface modifier adsorbed on the surface thereof with said cloud point modifier for a time and under conditions sufficient to form a nanoparticle containing an x-ray diagnostic compound, having a non-ionic surfactant as a surface modifier adsorbed on the surface thereof and a cloud point modifier associated therewith.

2. The method of claim 1 wherein said x-ray diagnostic compound is ethyl 3,5-diacetoamido-2,4,6-triiodobenzoate.

3. The method of claim 1 wherein said non-ionic surfactant is a poloxamine.

4. The method of claim 3 wherein said poloxamine is a tetrafunctional block copolymer derived from sequential addition of propylene oxide and ethylene oxide to ethylenediamine.

5. The method of claim 1 wherein said cloud point modifier is a phospholipid.

6. The method of claim 5 wherein said phospholipid is dimyristoyl phosphatidyl glycerol.

7. The method of claim 1 wherein said cloud point modifier is an anionic surfactant.

8. The method of claim 1 wherein said cloud point modifier is dioctylsulfosuccinate.

9. The method of claim 1 wherein said cloud point modifier is selected from the group consisting of polyethylene glycol, propylene glycol, ethanol, cyclodextrin, sodium dodecyl sulfate, dioctylsulfosuccinate, cetrimide, dimyristoylphosphatidylglycerol, cardiolipin and dimyristoylphosphatidylserine.

10. A method for making nanoparticles containing an x-ray diagnostic compound having nonionic poloxamine surfactant having a molecular weight of at least about 300,000 as a surface modifier adsorbed on the surface thereof comprised of contacting said nanoparticle containing an x-ray diagnosticle compound with said nonionic poloxamine surfactant for a time and under conditions sufficient to form a nanoparticle with a surface modifier adsorbed on the surface thereof.

11. The method of claim 10 further comprising the step of contacting said nanoparticle with said nonionic poloxamine surfactant adsorbed on the surface thereof with a cloud point modifier.

12. The method of claim 11 wherein said cloud point modifier is a phospholipid.

13. The method of claim 12 wherein said phospholipid is dimyristoyl phosphatidyl glycerol.

14. The method of claim 11 wherein said cloud point modifier is an anionic surfactant.

15. The method of claim 11 wherein said cloud point modifier is dioctylsulfosuccinate.

16. The method of claim 11 wherein said cloud point modifier is selected from the group consisting of polyethylene glycol, propylene glycol, ethanol, cyclodextrin, sodium dodecyl sulfate, dioctylsulfosuccinate, cetrimide, dimyristoylphosphatidylglycerol, cardiolipin and dimyristoylphosphatidylserine.

17. The method of claim 10 wherein said x-ray diagnostic compound is ethyl 3,5-diacetoamido-2,4,6-triiodobenzoate.

* * * * *